(12) United States Patent
Harada et al.

(10) Patent No.: US 7,891,814 B2
(45) Date of Patent: Feb. 22, 2011

(54) MENTAL FATIGUE DETECTING METHOD AND DEVICE

(75) Inventors: Nobuyoshi Harada, Ikeda (JP); Sunao Iwaki, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 12/624,067

(22) Filed: Nov. 23, 2009

(65) Prior Publication Data
US 2010/0085539 A1 Apr. 8, 2010

Related U.S. Application Data

(63) Continuation of application No. PCT/JP2008/057863, filed on Apr. 23, 2008.

(30) Foreign Application Priority Data

Jun. 5, 2007 (JP) .............................. 2007-148747

(51) Int. Cl.
*A61B 3/00* (2006.01)
*A61B 3/14* (2006.01)
(52) U.S. Cl. ........................ 351/246; 351/203; 351/206
(58) Field of Classification Search ................. 351/200, 351/203, 246
See application file for complete search history.

(56) References Cited

U.S. PATENT DOCUMENTS

| 5,187,506 A | 2/1993 | Carter |
| 6,702,757 B2 | 3/2004 | Fukushima et al. |
| 7,503,654 B2 | 3/2009 | Nakagawa |
| 2005/0200808 A1 | 9/2005 | Wyatt |
| 2007/0273611 A1 * | 11/2007 | Torch .............................. 345/8 |

FOREIGN PATENT DOCUMENTS

| JP | 06-500938 A | 2/1994 |
| JP | 07-111989 A | 5/1995 |

(Continued)

OTHER PUBLICATIONS

International Search Report of PCT/JP2008/057863, mailing date of May 27, 2008.

*Primary Examiner*—Joseph Martinez
*Assistant Examiner*—James R Greece
(74) *Attorney, Agent, or Firm*—Westerman, Hattori, Daniels & Adrian, LLP

(57) ABSTRACT

A mental fatigue detection device for detecting mental fatigue without arbitrariness using a flickering light includes: a light-emitting unit (1) for emitting a flickering visible light; a lighting unit (2) for emitting an infrared ray; an imaging unit (3) for taking an infrared image; and a control unit (4); wherein: the light-emitting unit (3) presents a test subject a flickering visible light with its frequency changing monotonically and stepwise; the imaging unit (3) captures an image of a region containing an eye of the test subject; the control unit (4) finds a pupil diameter of an image of the eye contained in each frame image of the captured image as time-series data, finds a threshold frequency of the test subject at the time of the measurement based on the variation in the pupil diameter and compares the threshold frequency with a threshold frequency when the test subject has no mental fatigue, thereby determining that whether the test subject has mental fatigue.

8 Claims, 5 Drawing Sheets

FOREIGN PATENT DOCUMENTS

| | | |
|---|---|---|
| JP | 07-255669 A | 10/1995 |
| JP | 2001-218756 A | 8/2001 |
| JP | 2001-309887 A | 11/2001 |
| JP | 2002-253509 A | 9/2002 |
| JP | 2003-070773 A | 3/2003 |
| JP | 2005-279053 A | 10/2005 |
| WO | 2005/096917 A1 | 10/2005 |

* cited by examiner

MENTAL FATIGUE DETECTING METHOD AND DEVICE

TECHNICAL FIELD

The present invention relates to mental fatigue detection, particularly to a mental fatigue detecting method and a device for detecting mental fatigue by observing changes in the pupils induced by the flickering of optical stimulation.

BACKGROUND ART

Appropriate management of physical and mental fatigue of laborers in diversified labor environments is indispensable in modern society not only to protect the laborer's own health but also to prevent accidents which can affect the laborer involved and other people, possibly the whole society. Hitherto, physical fatigue was evaluated relatively easily in reference to some external indices such as muscular weakness, whereas mental fatigue was evaluated mostly by carrying out surveys or the like. Therefore, it has always been difficult to exclude arbitrariness from mental fatigue evaluation.

A change in the threshold (may also be referred to as a flicker value) of the frequency at which the user can perceive the flickering of a flicker light is a known index of mental fatigue. This index is based on a decrease in the activity of the entire cerebral cortex, which is a major symptom of mental fatigue. The flicker of light flickering at a high speed is generally not perceived by a user; instead, the user perceives it as a constant illumination. As the flicker frequency is gradually decreased from a high value to a low value, the user perceives the flicker at a certain point. The frequency at which the user perceives the flicker is called a flicker frequency threshold or a flicker value. There is a known phenomenon in which the user becomes incapable of perceiving the flicker at a certain threshold frequency due to the accumulation of mental fatigue resulting from labor, even though the user was able to perceive it when he/she was in a general healthy condition (when the user had no mental fatigue). More specifically, the threshold frequency at which the user perceives the flicker, i.e., the flicker value, decreases due to mental fatigue.

Though they are not widely known, there are methods of evaluating mental activity, such as the degree of fatigue, by measuring the physiological reaction of the eyes, and a method of fatigue recovery by exposing the eyes to optical stimulation (see the following Patent Documents 1 to 3). However, a change in the activity of the entire cerebral cortex due to mental fatigue induced by various labor has been evaluated mostly by making the user subjectively determine the flicker perception threshold among variable flicker frequencies with a push-button operation or the like (for example, see the following Patent Documents 4 to 6).

[Citation List]

[Patent Document 1] Japanese Unexamined Patent Publication No. 7-255669

[Patent Document 2] Japanese Unexamined Patent Publication No. 2002-253509

[Patent Document 3] Japanese Unexamined Patent Publication No. 2005-279053

[Patent Document 4] Japanese Unexamined Patent Publication No. 2001-309887

[Patent Document 5] Japanese Unexamined Patent Publication No. 2001-218756

[Patent Document 6] Japanese Unexamined Patent Publication No. 2003-70773

SUMMARY OF INVENTION

Technical Problem

However, although the method of making the user subjectively determine the flicker perception threshold with a push-button operation or the like uses a physiological index, subjectivity is introduced during the final determination. Therefore, it is not possible to completely eliminate arbitrariness from the evaluation.

If the physiological reaction during the perception of the flickering of a flicker light can be detected without arbitrariness, it becomes possible to improve the accuracy of mental fatigue evaluation that is based on a change in the threshold of flicker perception. This also makes it possible to realize an unconstrained, non-contact, and nonarbitrary mental fatigue measurement method in which the laborer is subjected to measurement under natural conditions.

In order to solve the foregoing problems, an object of the present invention is to provide a mental fatigue detecting method and device which enable nonarbitrary detection of mental fatigue using a flickering light.

Solution to Problem

As a result of intensive study, the inventors of the present invention found that the state of mental fatigue of a person can be evaluated without arbitrariness by using the difference in the change in pupil diameter, and a brain potential reaction related to the change in pupil diameter, during a state of perception or non-perception of the flickering of flickering light. With this finding, the inventors completed the present invention.

Further, by combining the present invention with a notification means operated directly by the test subject, such as a push-button means, it becomes possible to prevent intentional or unintentional false measurement, enabling more accurate mental fatigue evaluation of the test subject. This is conducive to the improvement of job safety.

Specifically, a first mental fatigue detection method of the present invention, comprises the steps of:

a first step of presenting a flickering visible light to a test subject by varying a flicker frequency from a start frequency to an ending frequency monotonically and stepwise with time;

a second step of finding a pupil diameter of the test subject as time-series data during the presentation of the flickering visible light to the test subject;

a third step of repeating, for each shift of a predetermined period, an operation of finding a first standard deviation by finding a standard deviation of the time-series data of the pupil diameter within a first half of the predetermined period, and finding a second standard deviation by finding a standard deviation of the time-series data of the pupil diameter within a second half of the predetermined period;

a fourth step of finding an absolute value of a difference between the first standard deviation and the second standard deviation;

a fifth step of determining a maximum value among the plural absolute values;

a sixth step of finding a first frequency by finding a flicker frequency at a time of obtaining the pupil diameter used for calculation of the maximum value among the absolute values; and a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

A second mental fatigue detection method of the present invention comprises the steps of:

a first step of presenting a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;

a second step of finding a pupil diameter of the test subject during the presentation of the flickering visible light to the test subject;

a third step of finding, for the each second predetermined period, a maximum value Max of the pupil diameters which appears first after the second predetermined period and a minimum value Min of the pupil diameters which appears next to the maximum value Max;

a fourth step of finding, for the each second predetermined period, a mean value Base of the pupil diameters in a third period, which is a period residing before the second predetermined period;

a fifth step of finding a change rate using the corresponding ones of the maximum value Max, the minimum value Min, and the mean value Base, according to (Max−Base)/(Base−Min);

a sixth step of finding a timing where the change rate changes from a value equal to or greater than 1 to a value smaller than 1 or a timing where the change rate changes from a value equal to or smaller than 1 to a value greater than 1, and finding the flicker frequency corresponding to the timing, thereby finding a first frequency; and a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

A third mental fatigue detection method of the present invention comprises the steps of:

a first step of presenting a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;

a second step of finding a pupil diameter of the test subject during the presentation of the flickering visible light to the test subject;

a third step of finding, for the each second predetermined period, a standard deviation of the pupil diameters in a third period, which is a period residing before the second predetermined period;

a fourth step of finding an absolute value of a difference between two adjacent standard deviations among a time-series of the standard deviations;

a fifth step of determining a maximum value among the plural absolute values;

a sixth step of finding a first frequency by finding a flicker frequency at a time of obtaining the pupil diameter used for calculation of the maximum value among the absolute values; and a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

A fourth mental fatigue detection method of the present invention comprises the steps of:

a first step of presenting a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;

a second step of measuring a brain potential of the test subject during the presentation of the flickering visible light to the test subject;

a third step of finding, for the each second predetermined period, a maximum amplitude of the brain potential which appears first after the second predetermined period;

a fourth step of finding a change rate of a time-series of the maximum amplitudes;

a fifth step of determining a maximum value among the plural change rates;

a sixth step of finding a plurality of the flicker frequencies at the time of the measurement of the brain potential used for calculation of the maximum value among the change rates, and finding a first frequency using the flicker frequencies; and a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

A first mental fatigue detection device of the present invention comprises:

a light-emitting unit for emitting a flickering visible light;
an imaging unit for taking an infrared image; and
a control unit;
wherein:

the light-emitting unit presents a flickering visible light to a test subject by varying a flicker frequency from a start frequency to an ending frequency monotonically and stepwise with time;

the imaging unit captures an image of a region containing an eye of the test subject during the presentation of the flickering visible light to the test subject;

the control unit finds a pupil diameter of an image of the eye contained in each frame image of the captured images as time-series data, repeats, for each shift of a predetermined period, an operation of finding a first standard deviation by finding a standard deviation of the time-series data of the pupil diameter within a first half of the predetermined period and finding a second standard deviation by finding a standard deviation of the time-series data of the pupil diameter within a second half of the predetermined period, finds an absolute value of a difference between the first standard deviation and the second standard deviation, determines a maximum value among the plural absolute values, finds a first frequency by finding a flicker frequency at a time of obtaining the frame image used for calculation of the maximum value among the absolute values, and finds an absolute value of a difference between the first frequency and a second frequency, which is a flicker frequency threshold of the test subject when the test subject has no fatigue and determines that the test subject has mental fatigue when the absolute value is equal to or greater than a predetermined value.

A second mental fatigue detection device of the present invention comprises:
 a light-emitting unit for emitting a flickering visible light;
 an imaging unit for taking an infrared image; and
 a control unit;
 wherein:
  the light-emitting unit presents a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
  the imaging unit captures an image of a region containing an eye of the test subject during the presentation of the flickering visible light to the test subject;
  the control unit finds a pupil diameter of an image of the eye contained in each frame image of the captured images as time-series data,
  finds, for the each second predetermined period, a maximum value Max of the pupil diameters which appears first after the second predetermined period and a minimum value Min of the pupil diameters which appears next to the maximum value Max,
  finds, for the each second predetermined period, a mean value Base of the pupil diameters in a third period, which is a period residing before the second predetermined period,
  finds a change rate using the corresponding ones of the maximum value Max, the minimum value Min, and the mean value Base, according to (Max−Base)/(Base−Min),
  finds a timing where the change rate changes from a value equal to or greater than 1 to a value smaller than 1 or a timing where the change rate changes from a value equal to or smaller than 1 to a value greater than 1 and finds a flicker frequency corresponding to the timing, thereby finding a first frequency, and
  finds an absolute value of a difference between the first frequency and a second frequency, which is a flicker frequency threshold of the test subject when the test subject has no fatigue and determines that the test subject has mental fatigue when the absolute value is equal to or greater than a predetermined value.

A third mental fatigue detection device of the present invention comprises:
 a light-emitting unit for emitting a flickering visible light;
 an imaging unit for taking an infrared image; and
 a control unit;
 wherein:
  the light-emitting unit presents a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
  the imaging unit captures an image of a region containing an eye of the test subject during the presentation of the flickering visible light to the test subject;
  the control unit finds a pupil diameter of an image of the eye contained in each frame image of the captured images,
  finds, for the each second predetermined period, a standard deviation of the pupil diameters in a third period, which is a period residing before the second predetermined period,
  finds an absolute value of a difference between two adjacent standard deviations among a time-series of the standard deviations,
  determines a maximum value among the plural absolute values,
  finds a first frequency by finding a flicker frequency at a time of obtaining the frame image used for calculation of the maximum value among the absolute values, and
  finds an absolute value of a difference between the first frequency and a second frequency, which is a flicker frequency threshold of the test subject when the test subject has no fatigue and determines that the test subject has mental fatigue when the absolute value is equal to or greater than a predetermined value.

A fourth mental fatigue detection device of the present invention comprises:
 a light-emitting unit for emitting a flickering visible light;
 a brain potential measuring unit; and
 a control unit;
 wherein:
  the light-emitting unit presents a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
  the brain potential measuring unit measures a brain potential of a test subject during the presentation of the flickering visible light to the test subject;
  the control unit finds, for each second predetermined period, a maximum amplitude of the brain potential which appears first after the second predetermined period,
  finds a change rate of a time-series of the maximum amplitudes,
  determines a maximum value among the plural change rates,
  finds a plurality of the flicker frequencies at the time of the measurement of the brain potential used for calculation of the maximum value among the change rates and finds a first frequency using the flicker frequencies, and
  finds an absolute value of a difference between the first frequency and a second frequency, which is a flicker frequency threshold of the test subject when the test subject has no fatigue and determines that the test subject has mental fatigue when the absolute value is equal to or greater than a predetermined value.

Advantageous Effects of Invention

The method of the present invention allows for the determination of a flicker frequency threshold of a test subject without relying on subjective means such as a push-button operation, while eliminating intentional false measurements or arbitrariness from a test subject, with much less burden to the test subject, thereby evaluating the mental fatigue of the test subject based on a measured threshold.

Similarly, observation of a brain potential during the presentation of a flickering light also enables determination of a flicker frequency threshold of a test subject while eliminating intentional false measurements or arbitrariness from a test subject thereby evaluating the mental fatigue of the test subject based on a measured threshold.

Figure 1:
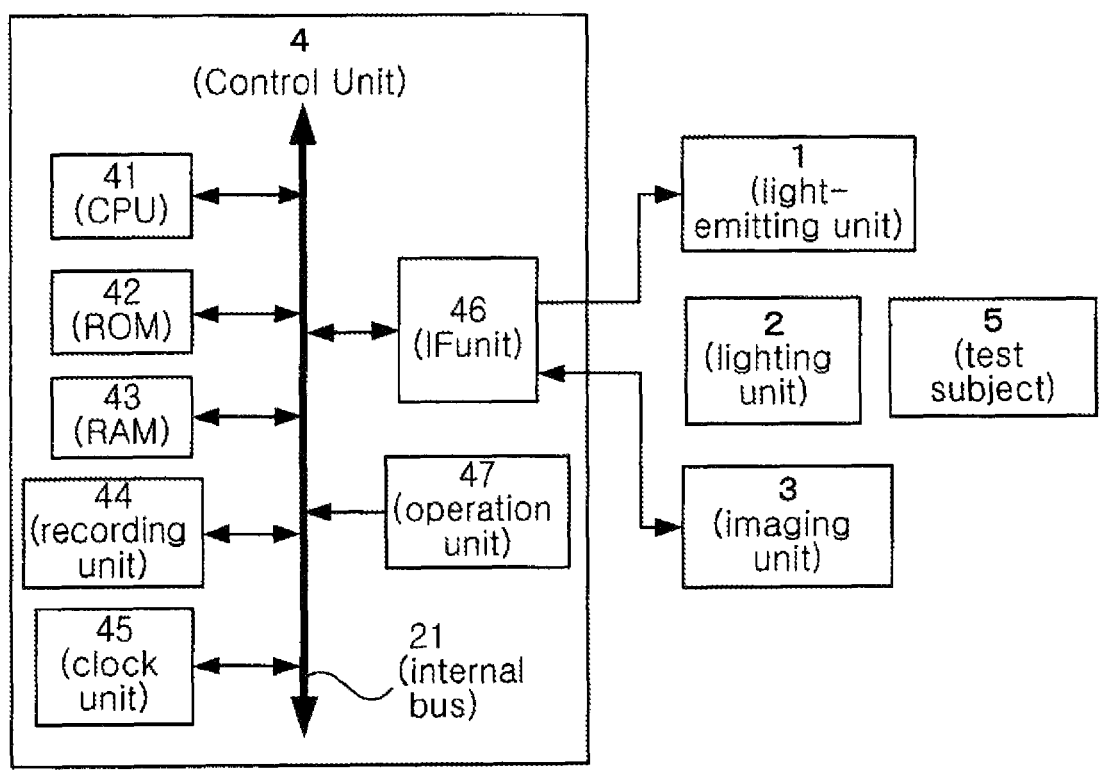
FIG. 1 is a block diagram illustrating the structure of a mental fatigue detecting device according to an embodiment of the present invention.

REFERENCE NUMERALS 1. light-emitting unit
2. lighting unit
3. imaging unit
4. control unit
5. test subject
41. arithmetic processing unit (CPU)
42. nonvolatile read-only memory (ROM)
43. volatile rewritable memory (RAM)
44. recording unit
45. clock unit
46. interface unit (IF unit)
47. operation unit

DESCRIPTION OF EMBODIMENTS

One embodiment of the present invention is described below with reference to the attached figures. Hereinafter, "fatigue" means mental fatigue, unless otherwise specified.

Figure 2:
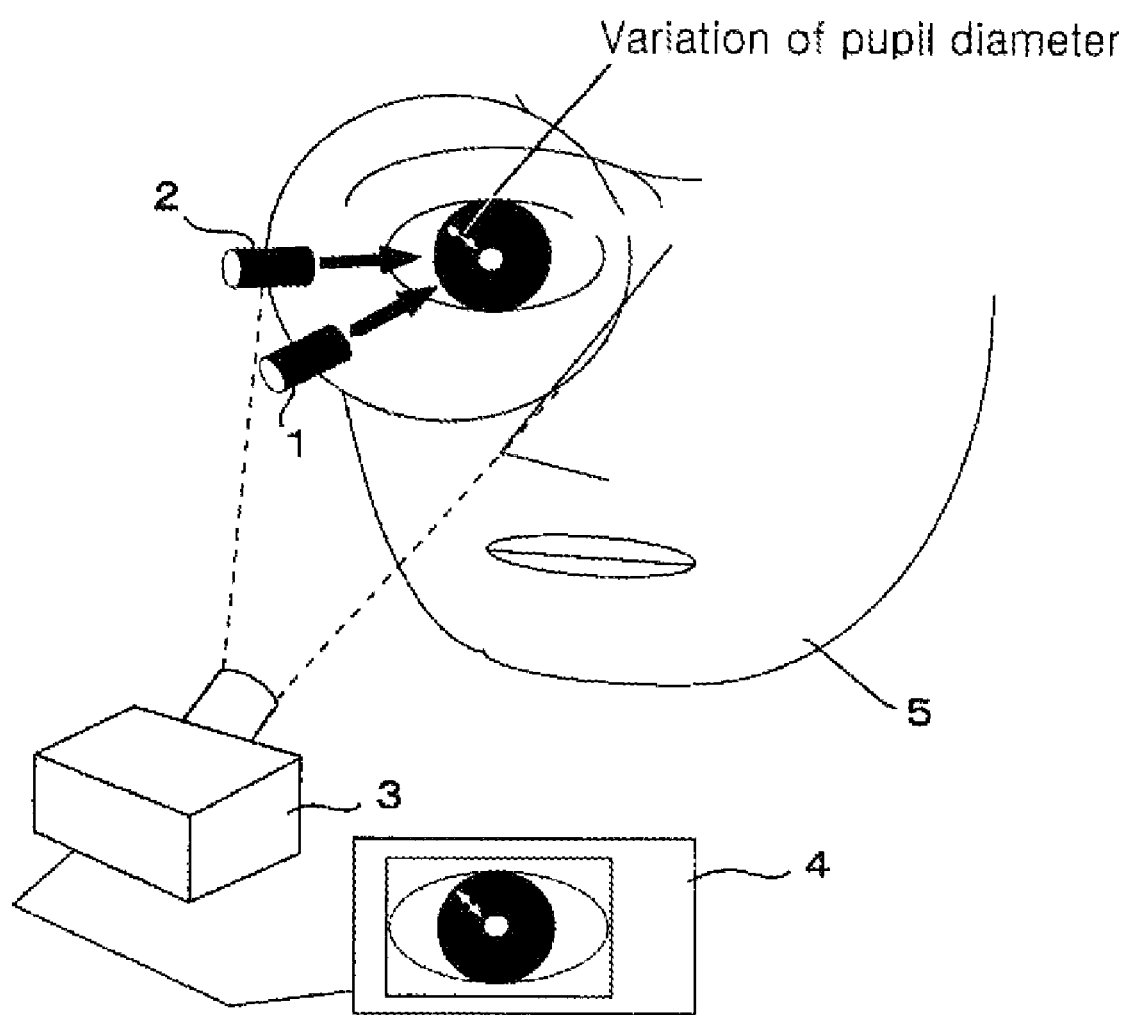
FIG. 2 is a perspective view illustrating relative positions of the mental fatigue detecting device shown in FIG. 1 and a test subject.

FIG. 1 is a block diagram illustrating the structure of a mental fatigue detecting device according to an embodiment of the present invention. The detecting device comprises a light-emitting unit 1 configured to emit a flickering visible light; a lighting unit 2 configured to emit an infrared ray; an imaging unit 3 sensitive to an infrared ray and configured to capture images (moving images); and a control unit 4 configured to analyze the images taken by the imaging unit 3 so as to detect mental fatigue. FIG. 1 also illustrates a test subject 5 undergoing mental fatigue detection. FIG. 2 is a perspective view illustrating the relative position of the mental fatigue detecting device and the test subject 5.

Under the control of the control unit 4, the light-emitting unit 1 emits visible light flickering at a predetermined frequency and strength. The light-emitting unit 1 comprises, for example, an LED and a driving unit for driving the LED. The light-emitting unit 1 is disposed within the field of vision of the test subject 5, and the flickering light emitted from the light-emitting unit 1 enters into the eyes of the test subject 5.

When the later-described measurement is performed while the test subject 5 is working, it is preferable to set the light-emitting unit 1 at about 10° from the center of the field of vision of the test subject 5 so that the measurement does not interrupt his/her work.

Under the control of the control unit 4, the imaging unit 3 captures an infrared ray image mainly consisting of an eye of the test subject 5. The imaging unit 3 transmits the infrared image to the control unit 4 as digital data. The imaging unit 3 is realized by, for example, a CCD camera. The lighting unit 2 irradiates the eye of the test subject 5 with an infrared ray at a frequency within the sensitivity range of the imaging device so as to allow the imaging unit 3 to capture an image of a desirable quality.

The control unit 4 includes an arithmetic processing unit (CPU, hereinafter) 41, a nonvolatile read-only memory (ROM, hereinafter) 42 for storing a program or the like, a volatile rewritable memory (RAM, hereinafter) 43 for temporarily storing data, a nonvolatile rewritable recording unit 44 for continuously storing data, a clock unit 45, an interface unit (IF unit, hereinafter) 46, and an operation unit 47. The control unit 4 is realized by, for example, a computer. The control unit 4 controls the light-emitting unit 1 and the imaging unit 3 via the IF unit 46. The image data transmitted from the imaging unit 3 to the control unit 4 is stored in the recording unit 44. The clock unit 45 is a means for outputting information of the current time using an internal clock such as a timer.

Figure 3:
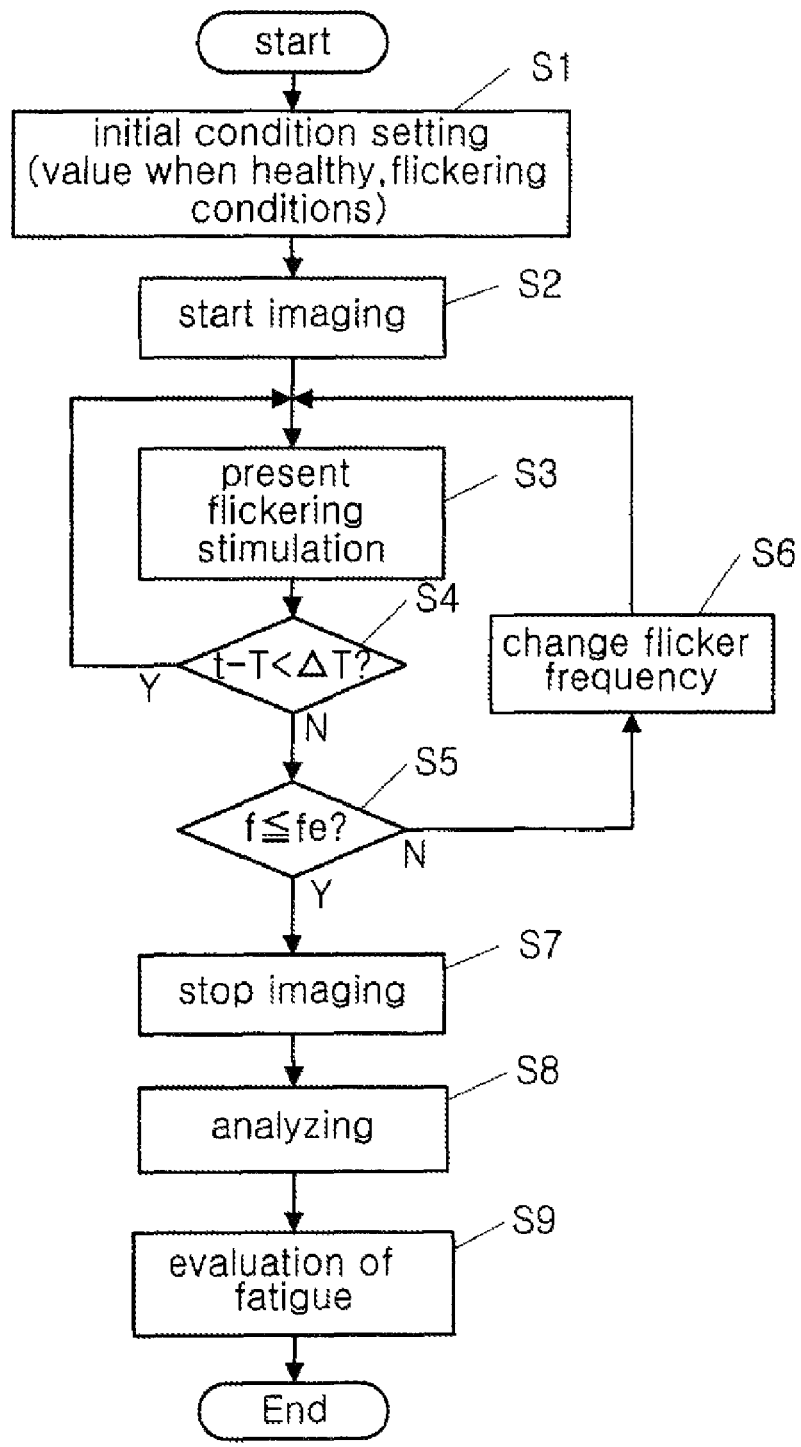
FIG. 3 is a flow chart showing a mental fatigue detecting method according to an embodiment of the present invention.

With reference to the flow chart in FIG. 3, the following describes the details of a mental fatigue detection method using the present detecting device. In the following description, all operations are carried out by a CPU 41, unless otherwise specified. The CPU 41 reads out necessary data from the ROM 42 and the recording unit 44 as required, processes the data using a predetermined area of the RAM 43 as working area, and stores the temporary results and the final processing results in the recording unit 44. The initial condition required for the measurement is previously stored in the recording unit 44.

First Mental Fatigue Detecting Method

In Step S1, as information about the test subject 5, a flicker frequency threshold f0 (Hz) in the state where the test subject has no subjective mental fatigue is stored via the operation unit 47. The CPU reads out frequency variation band fw(Hz), frequency increase amount Δf(Hz), and time difference ΔT(seconds) from the recording unit 44, thereby calculating a start frequency fs(=f0+fw) and ending frequency fe(=f0−fw). Then the start frequency fs is set as the flicker frequency f. The current time is acquired from the clock unit 45 to be used as a time parameter T so as to change, as described later, the flicker frequency f by a frequency difference Δf each time the time difference ΔT elapses.

For example, the values are set as: fw=10 (Hz), Δf=1 (Hz) and ΔT=2 (seconds). When 34 Hz is inputted as the threshold frequency f0 of the test subject 5, fs and fe become 44 Hz and 24 Hz, respectively.

In Step S2, in the state where the eyes of the test subject 5 are irradiated with the light of the infrared ray from the lighting unit 2, the imaging unit 3 is caused to capture an image of a region containing an eye of the test subject 5. The acquired image data is transmitted to the control unit 4, and is stored in the recording unit 44 as digital data.

In Step S3, using the current frequency f=fs determined in Step S1, the light-emitting unit 1 is commanded to emit a flickering light at a predetermined strength, at the flicker frequency f, and at duty=50%. When the light-emitting unit 1 is configured of an LED and an LED driving device, the CPU 41 transmits the flicker frequency f to the LED driving device at a predetermined timing. Receiving the flicker frequency f, the LED driving device applies a predetermined voltage, which changes at the flicker frequency f, to an LED so that the LED emits a flickering light. The voltage applied to the LED is, for example, a rectangular wave or a sine wave (cosine wave) at duty=50%.

In Step S4, the current time t is acquired from the clock unit 19 to be compared with the time parameter T, so as to determine whether their difference (t−T) is smaller than the time difference $\Delta T$ (t−T<$\Delta T$). Where t−T≧$\Delta T$, the sequence goes to Step S5.

In Step S5, a determination is carried out to determine whether the current flicker frequency f is smaller than the ending frequency fe (f≦fe). Where f>fe, the sequence goes to Step S6 to subtract the frequency difference $\Delta f$ from the current flicker frequency f to determine a new flicker frequency f (f=f−$\Delta f$). Then, after setting the current time t acquired in Step S4 as the time parameter T, the sequence goes to Step S3. This causes the LED to emit a flickering light at the new flicker frequency f. Where f≦fe, the sequence goes to Step S7 to stop light-emission by the light-emitting unit 1 and image-taking by the imaging unit 2.

Through Steps S2 to S6, the imaging unit 2 captures an image of a region containing an eye of the test subject 5 while the LED emits a flickering light, and the flicker frequency f is decreased stepwise from the start frequency fs to the ending frequency fe by subtracting the frequency difference $\Delta f$ each time the time $\Delta T$ elapses. Each image data is stored in the recording unit 44.

In Step S8, the series of moving image data stored in the recording unit 44 is processed frame by frame, thereby analyzing the change in pupil size.

Figure 4:
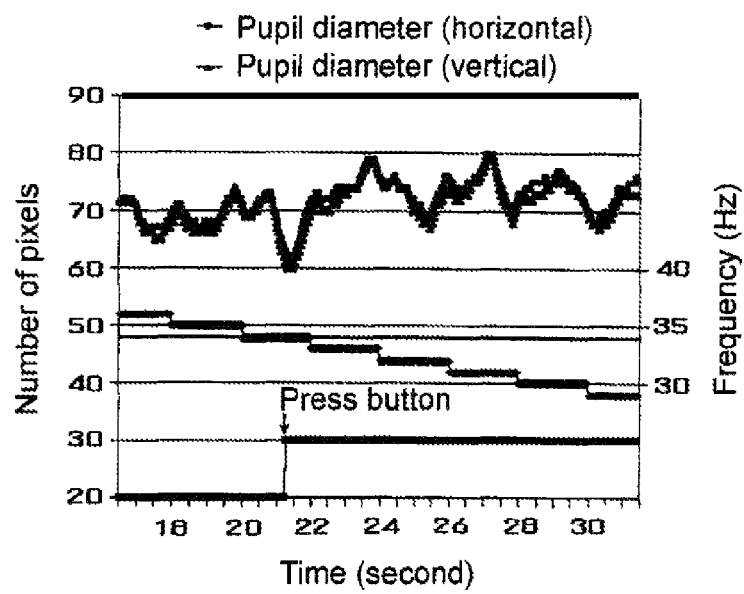
FIG. 4 is a graph showing a result of the observation of a change in pupil diameter while decreasing the flicker frequency.

First, the pupil area is detected by edge detection or the like for each frame image, thereby finding the diameter of the pupil (pupil diameter, hereinafter) by the number of pixels. The obtained pupil diameters are stored in the recording unit 44 as time-series data corresponding to the series of moving image data. FIG. 4 is a graph showing the obtained pupil diameters with the varied flicker frequencies. FIG. 4 separately displays a pupil diameter in the horizontal direction and a pupil diameter in the vertical direction; however, since they exhibit substantially the same change, only one of them (for example, vertical pupil diameter) is used in the following process. Since the calculation of pupil diameter can be performed by various image processing methods, the explanation is omitted.

Next, using the time-series data of pupil diameters obtained above, a standard deviation $\sigma 1$ of the pupil diameter in the first half of the continuing period (t1≦t<t1+5), and a standard deviation $\sigma 2$ of the pupil diameter in the second half of the continuing period (t1+5≦t<t1+10) are found for each of the predetermined continuing periods (for example, 10 seconds from t1 to t1+10), thereby finding an absolute value $\Delta\sigma(=|\sigma 1-\sigma 2|)$ of their difference. This process is carried out by shifting the continuing period (t1 to t1+10) by, for example, 1 second at a time.

Finally, the maximum value is found among the obtained absolute values $\Delta\sigma$ of the differences of the standard deviations of the pupil diameter, a time (t1+5) corresponding to the middle of the continuing period corresponding to the maximum value is calculated, and a flicker frequency f corresponding to the time is calculated. As described above, because the condition to control the flicker frequency is determined in advance, the flicker frequency at a given time can be determined as long as the time is informed. As mentioned later, the flicker frequency f (f1) thus obtained above corresponds to the threshold frequency of flicker at the time of measurement of the test subject 5.

In Step S9, the threshold frequency f1 found in Step S8 is compared with the threshold frequency f0(Hz) (the value in the state where the test subject 5 has no sense of mental fatigue) inputted in Step S1, thereby determining whether the test subject 5 has mental fatigue. Generally, it is known that the threshold frequency decreases if the test subject 5 has mental fatigue. More specifically, the threshold frequency is lower when a person has mental fatigue than when he has no mental fatigue. Therefore, when the difference between f1 and f0 (for example, absolute value|f1−f0|) is equal to or greater than a predetermined value, it is regarded that the test subject 5 has mental fatigue. The predetermined value to determine mental fatigue may be arbitrarily set to an appropriate value, for example, 5 Hz.

Accordingly, it becomes possible to automatically find the flicker frequency threshold to be used for the determination of mental fatigue of the test subjects, without demanding a determination about flicker perception from a test subject by using a push-button operation or the like.

Second Method for Detecting Mental Fatigue

Next, the following explains a second method for detecting mental fatigue. As with the first mental fatigue detection method, the second mental fatigue detection method also uses the detection device shown in FIG. 1, and carries out the same measurement. The second detection method differs from the first detection method in that the second detection method uses a different technique for flickering the light-emitting unit 1 and a different method for analyzing changes in pupil diameter. Therefore, the following mainly describes the differences from the first detection method.

First, the following details the conditions when the light-emitting unit 1 emits a flickering light. In Step S1 in FIG. 3, as with the first mental fatigue detection method, a flicker frequency threshold f0(Hz) of a test subject having no mental fatigue is provided as information regarding the test subject 5 via an operation unit. Further, a frequency variation band fw(Hz), a frequency increase amount $\Delta f$(Hz), an ON time $\Delta$ton, and OFF time $\Delta$toff, and a number of repetitions N are read out from the recording unit 14 to find a start frequency fs(=f0+fw) and an ending frequency fe(=f0−fw), and the start frequency fs is set as the flicker frequency f. As described later, the ON time $\Delta$ton represents a continuous time during which the light-emitting unit 1 emits a flickering light, and the OFF time $\Delta$toff represents a continuous time during which the light-emitting unit 1 does not emit light. The current time is obtained from the clock unit 45 to set the time as the time parameter T, thereby modifying the flicker frequency f by the frequency difference $\Delta f$ every time the time difference $\Delta T$ elapses. The time difference $\Delta T$ is found by ($\Delta$ton+$\Delta$toff)×N.

For example, the condition is set so that fw=7.5 (Hz), $\Delta f$=2.5 (Hz), $\Delta$ton=10 (seconds), $\Delta$toff=1.5 (seconds), and N=5. When f0=34 (Hz) is inputted under this condition, the condition becomes fs=41.5 (Hz), fe=26.5 (Hz), and $\Delta T$=(10+1.5)×5=57.5 (seconds), respectively.

The flickering of the light-emitting unit 1 is performed by the same operation as in Step S3 to S6; however, the above values ($\Delta T$, $\Delta f$, fe) are used for the timing for changing the flicker frequency f, the amount of variation, and the condition for ending the operation.

Figure 5:
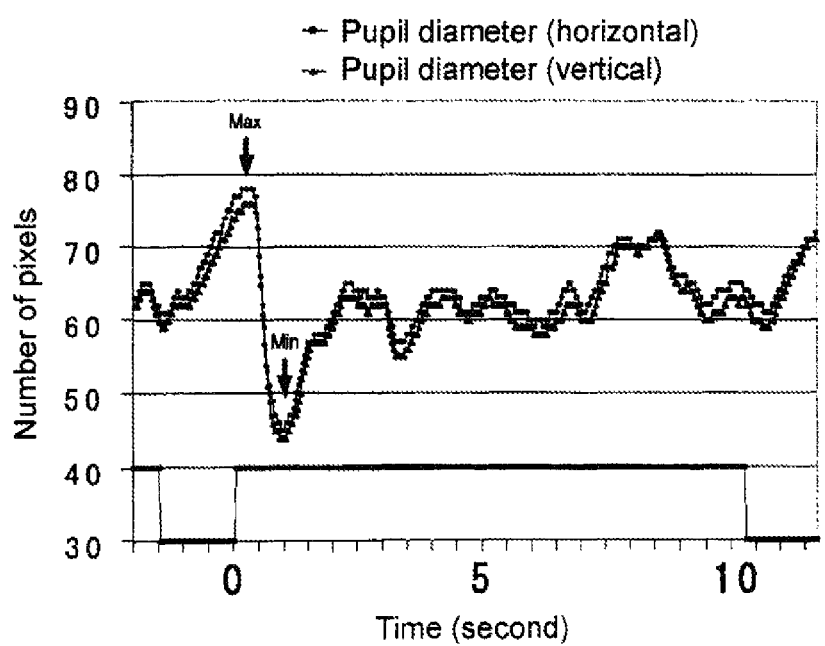
FIG. 5 is a graph showing a result of the observation of a change in pupil diameter in the operation of turning on and off a light flickering at a frequency at which the user can perceive a flicker.

The following describes Step S8 in which the series of moving image data stored in the recording unit 44 are processed frame by frame to analyze changes in pupil diameter. First, as in the first detection method, the image for each frame is processed to obtain time-series data of pupil diameter. FIG. 5 is a graph showing the obtained pupil diameter with varied flicker frequencies. As with FIG. 4, FIG. 5 separately displays a pupil diameter in the horizontal direction and a pupil diameter in the vertical direction; however, since they exhibit substantially the same change, only one of them (for example, vertical pupil diameter) is used in the following process. FIG. 5 is a graph of a part of the time-series data of pupil diameter, related to a specific flicker frequency f. It shows the change in pupil diameter within a single cycle of turning on and off a flickering light. The entire data of the change in pupil diameter are obtained in which similar data to that in FIG. 5 continues N times for each flickering frequency f.

Next, using the time-series data of pupil diameter, the variation range of pupil diameter during a change of the light-emitting unit 1 from the OFF state (no light emission) to ON state (flickering) is found. This change in pupil diameter, which is caused by switching from the OFF state to the ON state, is called a light stimulus omission reaction. As described later, as the flicker frequency is reduced, the enlargement tendency in pupil diameter due to the light stimulus omission changes to a contraction tendency in the vicinity of the reaction threshold frequency. To detect this change, the change rate r is found as follows.

As shown in FIG. 5, when the light-emitting unit 1 is switched from the OFF state to the ON state, the pupil diameter becomes maximum (denoted by "Max" in FIG. 5), and then immediately becomes minimum (denoted by "Min" in FIG. 5). Therefore, among the time-series data, an average of pupil diameters during a two second period before the specific omission reaction (two seconds before the OFF state begins), which is used as the reference value (may also be referred to as a base line) Base, is found. Then, the maximum value Max and the minimum value Min during the same omission reaction are found. Using these values, the change rate r=(Max−Base)/(Base−Min) is found. Using the time-series data of pupil diameter, the change rate r is found for each omission reaction. Then, an average value rav of change rates r corresponding to N measurements for each flicker frequency f is found.

Finally, the time where the obtained pupil diameter average change rate rav is changed from a value greater than 1 (the range of increase in the pupil diameter is greater than the range of decrease: enlargement tendency) to a value less than 1 (the range of increase in the pupil diameter is smaller than the range of decrease: contraction tendency) is found, and a flicker frequency f corresponding to this value is found. As described above, because the condition for controlling the flicker frequency is determined in advance, the flicker frequency at a given time can be determined as long as the time of the omission reaction is informed. The obtained flicker frequency f (referred to as f2) corresponds to the flicker frequency threshold of the test subject 5 at the time of measurement.

Step S9 carries out the same process as in the first detection method, i.e., a determination as to whether the test subject 5 has mental fatigue or not using the flicker perception frequency f2 calculated in Step S8. More specifically, if the difference between f2 and f0 (for example, absolute value|f2−f0|) is equal to or greater than a predetermined value, it is concluded that the test subject 5 has mental fatigue.

With this series of operations, it becomes possible to automatically find the flicker frequency threshold used for the determination of mental fatigue of the test subjects, without demanding a determination of flicker perception from the test subjects by using a push-button operation or the like.

The present invention is described above with references to a concrete embodiment; however, the present invention is not limited to the above embodiment, and may be varied in many ways.

For example, the light-emitting unit is not limited to LEDs and may be any device capable of emitting a flickering visible light at a predetermined frequency. The imaging unit is not limited to infrared ray imaging devices, and may be visible light imaging devices. Further, the lighting unit may be omitted.

The light-emitting unit, the imaging unit, and the lighting unit may be disposed in arbitrary positions, insofar as the measurement can be accurately performed. The imaging unit may be disposed in the vicinity of the test subject, or may be distant from the test subject. When it is distant, a telephoto lens may be used to capture an image.

Though the above embodiment adopts image processing to find a pupil diameter, the pupil diameter may be found in a method other than image processing. For example, the light reflected from the eyeball may be measured, and the pupil diameter may be found by utilizing the decrease in the amount of the light reflected as a result of an enlargement of the pupil. More specifically, while irradiating the eyes with a flickering light, the light reflected from the eyeball is measured plural times. Then, the variation in pupil diameter is found according to the measured values, and the result is processed as in the above, thereby automatically finding a flicker frequency threshold.

The present invention may serve as a mobile detection device. For example, the structure shown in FIG. 1 may be incorporated into a mobile phone. In this case, the test subject does not have to press the button to inform the perception while looking at the flicker light; the test subject merely has to look at the flicker light, and the device measures the change in pupil diameter, thereby estimating the degree of mental fatigue. A flickering light is emitted from a liquid crystal screen or LED, and an image of a pupil of the test subject looking at the flicker light is taken by a camera of the mobile phone. Then, the change in pupil diameter is found by using the measured pupil diameters or a change in brightness that reflects the pupil diameter.

Though the above embodiment explains a linear decrease of the flicker frequency, the present invention is not limited to this embodiment. For example, the flicker frequency may be linearly increased from a low frequency. Further, insofar as the change is monotonic, the frequency may be increased/decreased nonlinearly. In the second detection method, the flicker frequency is increased by detecting a change of the change rate rav from a value smaller than 1 (representing enlargement tendency) to a value greater than 1 (representing contraction tendency).

Though the above first detection method uses the condition where fw=10 (Hz), Δf=1 (Hz), and ΔT=2 (seconds), these values may be changed as necessary.

Though the above second detection method uses the condition where fw=10 (Hz), Δf=2.5 (Hz), Δton=10 (seconds), Δtoff=1.5 (seconds), and N=5, these values may be changed as necessary.

The above method sets the start frequency and the stop frequency for varying the flicker frequency based on the flicker frequency threshold of the test subject; however, a predetermined start frequency fs and stop frequency fe may be used because there is no significant difference among the threshold frequencies of individuals. For example, 20 Hz and 50 Hz can be used as the minimum frequency and the maximum frequency, respectively.

The above method finds a pupil diameter by temporarily storing the all items of image data acquired by the imaging unit, and then analyzing the data. However, it is also possible to find the pupil diameter for every frame or every several frames of the image(s) being captured, and store the diameters in order of the time.

The second detection method may be performed differently; for example, it is possible to find the flicker frequency threshold at the time of measurement of the test subject using the entire data of the change in pupil diameter. More specifically, firstly, the standard deviation of the pupil diameter during two seconds immediately before the optical stimulation is turned off is found for each presentation of optical stimulation, and the absolute value of the difference between adjacent standard deviations is found for the obtained time-series standard deviations, determines the maximum value among the absolute values, determines the time of the optical stimulation OFF corresponding to the maximum value, and determines the flicker frequency at the time as the threshold frequency. As described later, this is based on the fact that the standard deviation of pupil diameter in the period two seconds before the turning off of the optical stimulation varies greatly in the vicinity of the threshold frequency.

Alternatively, the flicker frequency threshold at the time of measurement of the test subject 5 may be found by presenting a flickering light using the same ON/OFF sequence of the optical stimulation used in the second detection method to the test subject, and observing a brain potential reaction (visually evoked brain potential reaction, hereinafter) related to the variation in pupil diameter. Unlike the detection device shown in FIG. 1, this detection device comprises a brain potential measuring device instead of the lighting unit 2 and the imaging unit 3. An electrode of the brain potential measuring device is set on the head of the test subject to measure a potential induced by the brain potential reaction. When the test subject receives the optical stimulation, a magnetoencephalographic response, a reaction in which the magnetic field in the brain changes, is generated. As described later, it was revealed that, in the visually evoked magnetoencephalographic reaction resulting from the continuing flicker light stimulation omission reaction, when the flicker frequency is lower than the threshold so that the test subject perceives the flicker, the OFF reaction of the omission reaction is small; and when the flicker frequency is higher than the threshold so that the test subject does not perceive the flicker, the OFF reaction of the omission reaction is large. It is also known that the activities of the magnetoencephalographic response and the brain potential reaction are induced from the same source, and therefore their activity strengths are deeply related to each other. Accordingly, it is considered that the same result as that for the visually evoked magnetoencephalographic response can be obtained during the visual evoked brain potential reaction. More specifically, in response to the flicker light stimulation, an ON reaction of brain potential in response to the turning on of the light and an OFF reaction of brain potential in response to the turning off of the light, are detected. The ON reaction is a reaction in response to a change in the light environment due to the presentation of light in the dark, and the OFF reaction is a reaction in response to a change in the light environment to the dark from a state adapted to light. In the case of the ON reaction, the condition of the dark state, i.e., the original state, is not variable, and thus the reaction will be constant. In contrast, the OFF reaction changes depending on the adaptation to the light, i.e., the degree of the adaptation. That is to say, a greater OFF reaction can be detected in a state with a greater brightness, a greater stability, and a longer duration of adaptation to the light.

In this mental fatigue detection method using a brain potential reaction, the brightness of the light and the time for presenting the light are constant for each condition, whereas the light environment stability, i.e., the flicker frequency of the light is varied. The test subject will find it more difficult to perceive the flicker as the flicker frequency goes further above the flicker threshold. In this state, since the light environment becomes more stable and the adaptation of the test subject to the light is increased, a greater OFF reaction is obtained. Conversely, the test subject will find it easier to perceive the flicker as the flicker frequency falls further below the flicker threshold. In this state, since the light environment becomes more unstable, and the adaptation of the test subject to the light is hindered, a smaller OFF reaction is obtained. The magnitude of the OFF reaction is considered to represent a degree of adaptation of a test subject to light environment. A test subject starting to perceive a flicker is equivalent to a fact that light environment starts to be unsteady to the test subject, that is, the adaptation of the test subject starts to be hindered, and as a result of it, the OFF reaction becomes weak.

The following describes an embodiment of this method. For example, six different flicker frequencies are set, beginning at 35 Hz, with a 5 Hz increase before each additional stage, until 60 Hz (35, 40, 45, 50, 55 and 60 Hz). The flicker light stimulation is presented plural times for each of the determined flicker frequencies in ascending or descending order, and time-series data of the brain potential is measured. For the waveforms obtained by showing flicker light stimulation of the same frequency among all the waveform data, the brain potential data at the same timings within the ON/OFF sequence are averaged to find an averaged waveform of brain potentials. This process is carried out for each of the determined flicker frequencies. Then, the variation in amplitude of the OFF reaction with respect to the averaged waveform is evaluated to find the flicker frequency threshold. Because the amplitude of the OFF reaction is small at a frequency lower than the threshold, and is large at a frequency higher than the threshold, the flicker frequency threshold can be found by finding either a change in the amplitude of the OFF reaction from relatively greater to relatively smaller (when the flicker frequency is decreased), or a change from relatively smaller to relatively greater (when the flicker frequency is increased). For example, the flicker frequency threshold can be found by finding the absolute value of the amplitude differences between adjacent flicker frequencies with respect to the amplitudes of the OFF reaction obtained by decreasing the flicker frequency, and then finding the maximum value of the absolute values. For example, the flicker frequency threshold can be determined by finding an average value of the two flicker frequencies at which two items of data for calculating the maximum absolute value were found. Many other methods may be used to find flicker frequency threshold from the change in the amplitude of the OFF reaction.

If the threshold of the test subject in a general healthy condition is known, the threshold can be more accurately detected by setting the frequencies with smaller differences for the lower frequency range in the vicinity of the threshold. Further, if the noise characteristic etc. of the test subject is known, the averaged waveform can be found with a smaller number of additions, and therefore the detection of the threshold can be performed with more predetermined frequencies.

It is not always necessary to perform averaging. For example, though the waveform of the brain potential or the evoked reaction of a brain magnetic field due to external stimulation is typically found by averaging, a single reaction to a single individual stimulation can be detected without averaging, by appropriately designing a noise attenuating filter according to the characteristics of waveforms of the evoked response and the data of background noise and applying this filter to the measurement data. A method using a wavelet variable, which is one of the time-frequency analysis methods serving as a filter, is applicable for the detection of a single reaction to a single stimulation. Adoption of the noise attenuating filter to the evaluation of the flicker stimulation OFF reaction enables detection of a reaction to an individual stimulation, thereby allowing detection of the flicker reaction from the change of the OFF reaction at continuously varied frequencies.

The following describes experiment examples to prove the efficacy of the present invention.

Example 1

The first experiment was performed according to the first detection method. Under the flicker stimulation condition of fw=10 (Hz), $\Delta f$=1 (Hz), $\Delta T$=2 (seconds), as well as light on (50%) and light off (50%), flicker perception and changes in pupil diameter due to a decrease in the flicker light frequency are observed. Before the experiment, the threshold frequency f0 of the test subject under the above conditions was measured. The result was 34 Hz. Based on this result, the flicker frequency was continuously decreased from the threshold frequency 34 Hz+10 Hz (44 Hz: condition in which the test subject does not perceive the flicker) to the threshold frequency 34 Hz-10 Hz (24 Hz: condition in which the test subject perceives the flicker). The frequency was decreased every two seconds by 1 Hz for about 40 seconds. Images of a pupil of the test subject were taken during this process. Using the obtained data, changes in the number of pixels of the pupil diameter in the vertical direction and the horizontal direction were found. Concurrently, the test subject was instructed to press a button when he starts to perceive the flicker.

This experiment was performed using a FreeView DTS, an eye movement tracking apparatus, and eye movement statistical program II (products of Takei Scientific Instruments Co., Ltd.). The detection of the pupil from the captured image and the calculation of pupil diameter were performed using the image processing function of the program. For example, the extraction of the pupil was performed by image processing methods such as pattern matching based on a normalized correlation method, and automatic setting of threshold value based on discriminant analysis method, or the like.

FIG. 4 shows the result. In FIG. 4, the top waveform represents changes in pupil diameter. The staircase waveform in the middle represents changes in flicker frequency. The staircase waveform on the bottom represents the timing where the test subject presses a button to inform of perception of the flicker. The test subject pressed the button to inform the perception of the flicker at 34 Hz, which was the threshold frequency calculated before the experiment. Although the pupil diameter showed changes at the frequency of 34 Hz or greater, the changes were small. In contrast, when the frequency fell below 34 Hz, the observed changes in pupil diameter were significant.

A square mean value of the variation amount with respect to the mean value of the pupil diameters, i.e., standard deviation of the amplitudes was found for the period five or more seconds before the test subject pressed the button and a period five or more seconds after the push-button action. The standard deviations of pupil diameters in the periods five seconds before and after the push-button action from six examples were compared with each other. Because the change in pupil diameter in the vertical direction and the horizontal direction were substantially the same, the evaluation was performed using the pupil diameter (pixel number) in the vertical direction. According to the result, the mean value of the standard deviations of pupil variations was 2.48±0.29 pixels in the period five seconds before the push-button action, and was 4.06±0.34 pixels in the period five seconds after the push-button action. As a result of t-test, it was revealed that the standard deviation of the amplitudes was greater in the period five seconds after the push-button action than in the period five seconds before the push-button action at a significance level p=0.0012. More specifically, because the range of variation of pupil diameter greatly changes at the frequencies in the vicinity of the flicker frequency threshold, the flicker frequency threshold can be determined by observing the change in the standard deviations of the variations in pupil diameter.

Example 2

An experiment according to the second detection method was performed. Two values, a frequency (a frequency at which the flicker is not perceived) that is 7.5 Hz higher than the flicker perception threshold frequency and a frequency (a frequency at which the flicker is perceived) that is 7.5 Hz lower than the flicker perception threshold frequency, were used as the flicker frequency f. Every 10 seconds of the light (flicker) stimulation ON time ($\Delta$ton) is followed by 1.5 seconds of the light (flicker) stimulation OFF time ($\Delta$toff). This experiment observes changes in pupil diameter resulting from the on/off operations of the light stimulation before and after the 1.5 second period. As in Example 1, the flicker frequency threshold of the test subject measured before the experiment was 34 Hz, and therefore the flicker frequency at which the flicker is not perceived was set to 41.5 Hz, and the flicker frequency at which the flicker is perceived was set to 26.5 Hz. The imaging of the pupil and the calculation of pupil diameter were performed by the same apparatus and the same program as in Example 1.

Figure 6:
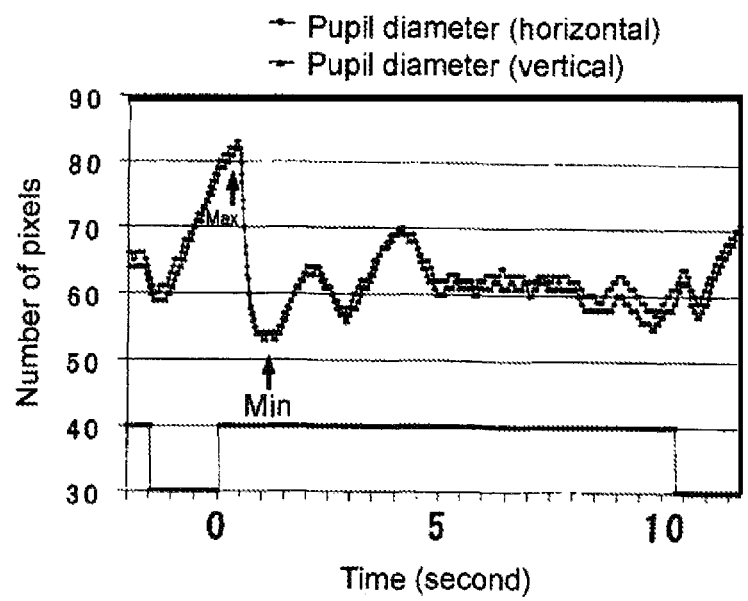
FIG. 6 is a graph showing a result of the observation of a change in pupil diameter in the operation of turning on and off a light flickering at a frequency at which the user cannot perceive a flicker.

FIGS. 5 and 6 show the results. FIGS. 5 and 6 show the case where the flicker frequency is 26.5 Hz and the case where the flicker frequency is 41.5 Hz, respectively.

Result 1: Stabilization process of pupil variation through optical stimulation omission reaction to stationary optical stimulation state Throughout the optical stimulation OFF state to the optical stimulation ON state, a rapid enlargement of a pupil in response to the turning off of a light and a rapid contraction of a pupil in response to the turning on of a light were observed. After about five seconds, the pupil began to stabilize in the condition in which the test subject did not perceive the flicker (41.5 Hz); in contrast, although the pupil began to stabilize to some extent, the variation was still observed at the condition in which the test subject perceived the flicker (26.5 Hz). Based on this result, the root mean square values of the differences from the average amplitude of the pupil variation, i.e., the standard deviations in the later half of the optical stimulation ON time, more specifically, in the two second period before turning off the optical stimulation were compared with each other for the condition in which the test subject perceived the flicker and for the condition in which the test subject did not perceive the flicker. Because the change in pupil diameter in the vertical direction and the horizontal direction were substantially the same, the evaluation was performed using the pupil diameter in the vertical direction. Five examples were compared. According to the result, the mean value of the standard deviations of pupil variations were 1.98±0.36 pixels in the condition in which the test subject does not perceive the flicker, and 3.09±0.36 pixels in the condition in which the test subject perceives the flicker. As a result of a t-test, it was revealed that the standard deviation of the amplitude was greater in the condition in which the test subject perceives the flicker than in the condition in which the test subject does not perceive the flicker with a significance level p=0.003.

This shows that, in the stabilization process of pupil variation associated with light omission stimulation, i.e., on/off of light stimulation, the condition in which the test subject perceives the flicker is less stable than the condition in which the test subject does not perceive the flicker; in other words, the condition in which the test subject perceives the flicker is likely to continue to be in an unstable state. Accordingly, by using optical stimulation comprised of continuous flicker light stimulation and omission while varying the flicker frequency stepwise, and observing the stabilizing process of the pupil variation, it is possible to determine whether the test subject actually perceives the flicker light.

Result 2: Pupil variation in omission reaction induced by optical stimulation sequence with higher/lower frequencies than flicker threshold.

When the optical stimulation is turned off or turned on during the 1.5 second period, a rapid enlargement of the pupil due to the turning off of the optical stimulation and a rapid contraction of pupil due to the turning on of the optical stimulation were observed. As evident from FIGS. 5 and 6, the pupil reaction in response to the omission of optical stimulation differs between the condition in which the test subject perceives the flicker (26.5 Hz) and the condition in which the test subject does not perceive the flicker (41.5 Hz). To prove this, using data of six sequences, a zero base pupil diameter is defined based on the data taken during the 1.5 seconds before the optical stimulation omission. Using this zero base, the degree of enlargement or contraction of the pupil diameter from the zero base resulting from the omission was found.

First, the degree of increase of pupil diameter from the zero base due to omission was found for each of the conditions in which the test subject perceives the flicker and the conditions in which the test subject does not perceive the flicker. As a result, the increase was 13.83±0.91 pixels in the condition in which the test subject perceives the flicker, and 19.83±1.25 pixels in the condition in which the test subject does not perceive the flicker. As a result of t-test, it was revealed that the pupil enlargement from the zero base in the condition in which the test subject does not perceive the flicker statistically showed more significant amplitude than in the condition in which the test subject perceives the flicker at a significance level p=0.0015.

Next, the pupil contraction reaction induced by the turning on of the optical stimulation subsequent to the increase of the pupil diameter induced by the turning off of the optical stimulation was found by finding the decrease from the zero base. The decrease was found for each of the condition in which the test subject perceives the flicker and the condition in which the test subject does not perceive the flicker. As a result, the decrease was 16.67±1.15 pixels in the condition in which the test subject perceives the flicker, and 10.17±1.30 pixels in the condition in which the test subject does not perceive the flicker. As a result of a t-test, it was revealed that the pupil contraction from the zero base in the condition in which the test subject does not perceive the flicker statistically showed less significant amplitude than in the condition in which the test subject perceives the flicker at a significance level p=0.0018.

The above tests showed that, the degree of pupil enlargement was greater, and the degree of pupil contraction was smaller in the condition in which the test subject does not perceive the flicker than in the condition in which the test subject perceives the flicker. In other words, the variations in pupil diameter in those conditions are such that the pupil variation has a contraction tendency in the condition in which the test subject perceives the flicker, and the pupil variation has an enlargement tendency in the condition in which the test subject does not perceive the flicker.

Therefore, as explained in the above second detection method, by presenting the test subject the optical stimulation sequence comprising of the flicker light stimulation sequence and omission, decreasing the frequency of the stimulation sequence stepwise, and observing the range of variation of the enlargement and contraction of the pupil due to the omission, it is possible to determine the frequency at which the test subject starts perceiving the flicker.

Example 3

The following describes a result of an experiment of a visually evoked magnetoencephalographic reaction. As stated below, it is considered that a similar result can also be obtained from a visually evoked brain potential reaction.

The flicker of light was presented in the following sequence. First, a flicker signal was turned on and maintained for 1500 ms, and then omission of the light is maintained for 1500 ms; thereafter, another flicker signal at a different frequency was turned on and maintained for 1500 ms. A flickering signal which turns on and off at an interval of 1500 ms was presented to the test subject at varied flicker frequencies, thereby finding the flicker frequency threshold of the test subject. Based on the obtained frequency threshold, the frequencies of the flickering signal to be presented were determined. More specifically, the light flicker frequencies were determined to be two high frequencies 2.5 Hz and 7.5 Hz higher than the threshold frequency at which the test subject cannot easily perceive the flicker, and two low frequencies 2.5 Hz and 7.5 Hz lower than the threshold frequency at which the test subject can perceive the flicker with relative ease. Four flicker stimulations of different frequencies are randomly presented 100 times in total while providing an optical stimulation omission time of 1500 ms therebetween.

Figure 7:
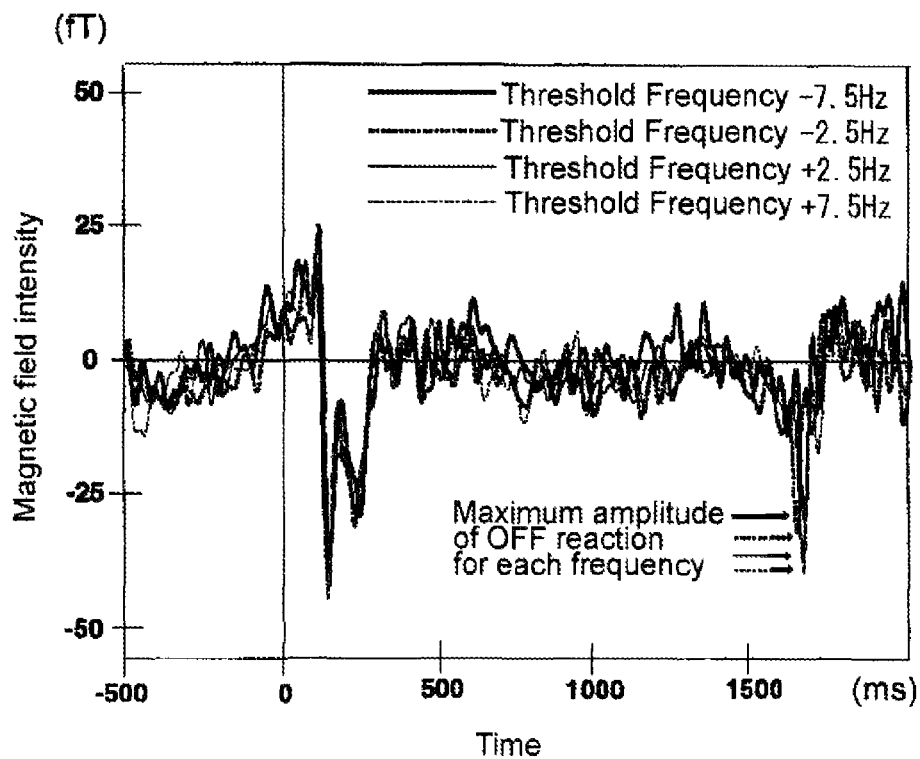
FIG. 7 is a graph showing a magnetoencephalography measured by presenting a flickering light being turned on and off to a test subject.

With the above four frequencies, visually evoked magnetoencephalographic reactions corresponding to the ON and OFF of the optical stimulation sequence were observed in the channel corresponding to the occipital primary visual area. FIG. 7 shows the obtained waveform data. In FIG. 7, the unit of the magnetic field intensity of the vertical axis is fT (femto Tesla). The four arrows in the lower right of the graph denote the positions of the maximum amplitudes of the OFF reactions with respect to the four frequencies.

By providing the flicker light stimulation, a magnetencephalographic ON reaction was detected in response to turning on the light, and a magnetoencephalography OFF reaction was detected in response to the turning off the light. The ON reaction is a reaction to a change in the light environment from the dark state for 1500 ms to a state where the light is presented. The OFF reaction is a reaction to a change in the light environment from the state adapted to light for 1500 ms to the dark state. There was no significant difference in the ON reaction between the above four frequencies. However, a great OFF reaction was observed at a frequency 2.5 Hz and 7.5 Hz higher than the threshold frequency, and a small OFF reaction was observed at a frequency 2.5 Hz and 7.5 Hz lower than the threshold frequency. As shown in FIG. 7, the order of the frequencies from the threshold frequency in terms of the size of variation during the OFF reaction was +7.5 Hz, +2.5 Hz, −2.5 Hz, and −7.5 Hz.

As such, a greater OFF reaction was observed at a higher frequency than the threshold frequency, compared with a lower frequency than the threshold frequency. At a higher frequency than the threshold frequency, the adaptation to the optical steady state advances more; this is apparently why the greater OFF reaction was detected in response to turning off the light. At a lower frequency than the threshold frequency, the adaptation to the optical steady state is insufficient, and the OFF reaction was not very great. As is evident from the result, in the visually evoked magnetoencephalographic OFF reaction to a flicker light stimulation sequence, the inhibition of adaption to the optically steady state corresponding to flicker perception was detected as a decrease in the amplitude of the OFF reaction.

The result shows that the reaction, which is the perception of flickering of flicker light, directly influences the activity of the cerebral cortex primary visual area; in other words, the reaction itself is an immediate reflection of the activity of the cerebral cortex. Accordingly, by observing not only the variation in pupil diameter, but also visually evoked magnetoencephalographic OFF reaction or brain potential diagram OFF reaction to flicker light stimulation sequence, it is possible to monitor the state where the test subject perceives the flickering of flicker light.

INDUSTRIAL APPLICABILITY

The method of the present invention allows for determination of the flicker frequency threshold of a test subject without relying on subjective means such as a push-button operation. The method thereby reduces the burden to the test subject and eliminates intentional false measurement or arbitrariness of the test subject. Using the obtained flicker frequency threshold, the method of the present invention enables evaluation of mental fatigue of the test subject.

The invention claimed is:

1. A mental fatigue detection method, comprising the steps of:
   a first step of presenting a flickering visible light to a test subject by varying a flicker frequency from a start frequency to an ending frequency monotonically and stepwise with time;
   a second step of finding a pupil diameter of the test subject as time-series data during the presentation of the flickering visible light to the test subject;
   a third step of repeating, for each shift of a predetermined period, an operation of finding a first standard deviation by finding a standard deviation of the time-series data of the pupil diameter within a first half of the predetermined period, and finding a second standard deviation by finding a standard deviation of the time-series data of the pupil diameter within a second half of the predetermined period;
   a fourth step of finding an absolute value of a difference between the first standard deviation and the second standard deviation;
   a fifth step of determining a maximum value among the plural absolute values;
   a sixth step of finding a first frequency by finding a flicker frequency at a time of obtaining the pupil diameter used for calculation of the maximum value among the absolute values; and
   a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

2. A mental fatigue detection method, comprising the steps of:
   a first step of presenting a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
   a second step of finding a pupil diameter of the test subject during the presentation of the flickering visible light to the test subject;
   a third step of finding, for the each second predetermined period, a maximum value Max of the pupil diameters which appears first after the second predetermined period and a minimum value Min of the pupil diameters which appears next to the maximum value Max;
   a fourth step of finding, for the each second predetermined period, a mean value Base of the pupil diameters in a third period, which is a period residing before the second predetermined period;
   a fifth step of finding a change rate using the corresponding ones of the maximum value Max, the minimum value Min, and the mean value Base, according to (Max−Base)/(Base−Min);
   a sixth step of finding a timing where the change rate changes from a value equal to or greater than 1 to a value smaller than 1 or a timing where the change rate changes from a value equal to or smaller than 1 to a value greater than 1, and finding the flicker frequency corresponding to the timing, thereby finding a first frequency; and
   a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

3. A mental fatigue detection method, comprising the steps of:
   a first step of presenting a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
   a second step of finding a pupil diameter of the test subject during the presentation of the flickering visible light to the test subject;
   a third step of finding, for the each second predetermined period, a standard deviation of the pupil diameters in a third period, which is a period residing before the second predetermined period;
   a fourth step of finding an absolute value of a difference between two adjacent standard deviations among a time-series of the standard deviations;
   a fifth step of determining a maximum value among the plural absolute values;
   a sixth step of finding a first frequency by finding a flicker frequency at a time of obtaining the pupil diameter used for calculation of the maximum value among the absolute values; and a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

4. A mental fatigue detection method, comprising the steps of:
a first step of presenting a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
a second step of measuring a brain potential of the test subject during the presentation of the flickering visible light to the test subject;
a third step of finding, for the each second predetermined period, a maximum amplitude of the brain potential which appears first after the second predetermined period;
a fourth step of finding a change rate of a time-series of the maximum amplitudes;
a fifth step of determining a maximum value among the plural change rates;
a sixth step of finding a plurality of the flicker frequencies at the time of the measurement of the brain potential used for calculation of the maximum value among the change rates, and finding a first frequency using the flicker frequencies; and
a seventh step of finding an absolute value of a difference between the first frequency and a second frequency, which is a flicker frequency threshold of the test subject when the test subject has no fatigue, and determining that the test subject has mental fatigue when the absolute value is equal to or greater than a predetermined value.

5. A mental fatigue detection device, comprising:
a light-emitting unit for emitting a flickering visible light;
an imaging unit for taking an infrared image; and
a control unit;
wherein:
the light-emitting unit presents a flickering visible light to a test subject by varying a flicker frequency from a start frequency to an ending frequency monotonically and stepwise with time;
the imaging unit captures an image of a region containing an eye of the test subject during the presentation of the flickering visible light to the test subject;
the control unit finds a pupil diameter of an image of the eye contained in each frame image of the captured images as time-series data,
repeats, for each shift of a predetermined period, an operation of finding a first standard deviation by finding a standard deviation of the time-series data of the pupil diameter within a first half of the predetermined period and finding a second standard deviation by finding a standard deviation of the time-series data of the pupil diameter within a second half of the predetermined period,
finds an absolute value of a difference between the first standard deviation and the second standard deviation,
determines a maximum value among the plural absolute values,
finds a first frequency by finding a flicker frequency at a time of obtaining the frame image used for calculation of the maximum value among the absolute values, and
finds an absolute value of a difference between the first frequency and a second frequency, which is a flicker frequency threshold of the test subject when the test subject has no fatigue and determines that the test subject has mental fatigue when the absolute value is equal to or greater than a predetermined value.

6. A mental fatigue detection device, comprising:
a light-emitting unit for emitting a flickering visible light;
an imaging unit for taking an infrared image; and
a control unit;
wherein:
the light-emitting unit presents a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;
the imaging unit captures an image of a region containing an eye of the test subject during the presentation of the flickering visible light to the test subject;
the control unit finds a pupil diameter of an image of the eye contained in each frame image of the captured images as time-series data,
finds, for the each second predetermined period, a maximum value Max of the pupil diameters which appears first after the second predetermined period and a minimum value Min of the pupil diameters which appears next to the maximum value Max,
finds, for the each second predetermined period, a mean value Base of the pupil diameters in a third period, which is a period residing before the second predetermined period,
finds a change rate using the corresponding ones of the maximum value Max, the minimum value Min, and the mean value Base, according to (Max−Base)/(Base−Min),
finds a timing where the change rate changes from a value equal to or greater than 1 to a value smaller than 1 or a timing where the change rate changes from a value equal to or smaller than 1 to a value greater than 1 and finds a flicker frequency corresponding to the timing, thereby finding a first frequency, and
finds an absolute value of a difference between the first frequency and a second frequency, which is a flicker frequency threshold of the test subject when the test subject has no fatigue and determines that the test subject has mental fatigue when the absolute value is equal to or greater than a predetermined value.

7. A mental fatigue detection device, comprising:
a light-emitting unit for emitting a flickering visible light;
an imaging unit for taking an infrared image; and
a control unit;
wherein:
the light-emitting unit presents a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;

the imaging unit captures an image of a region containing an eye of the test subject during the presentation of the flickering visible light to the test subject;

the control unit finds a pupil diameter of an image of the eye contained in each frame image of the captured images, finds, for the each second predetermined period, a standard deviation of the pupil diameters in a third period, which is a period residing before the second predetermined period, finds an absolute value of a difference between two adjacent standard deviations among a time-series of the standard deviations, determines a maximum value among the plural absolute values, finds a first frequency by finding a flicker frequency at a time of obtaining the frame image used for calculation of the maximum value among the absolute values, and finds an absolute value of a difference between the first frequency and a second frequency, which is a flicker frequency threshold of the test subject when the test subject has no fatigue and determines that the test subject has mental fatigue when the absolute value is equal to or greater than a predetermined value.

8. A mental fatigue detection device, comprising:

a light-emitting unit for emitting a flickering visible light;

a brain potential measuring unit; and a control unit;

wherein:

the light-emitting unit presents a flickering visible light to a test subject by repeating 1) a first predetermined period in which a flickering light is presented, and 2) a second predetermined period subsequent to the first predetermined period in which the presentation of a flickering light is suspended, while varying a flicker frequency from a start frequency to an ending frequency monotonically and stepwise with time;

the brain potential measuring unit measures a brain potential of a test subject during the presentation of the flickering visible light to the test subject;

the control unit finds, for each second predetermined period, a maximum amplitude of the brain potential which appears first after the second predetermined period, finds a change rate of a time-series of the maximum amplitudes, determines a maximum value among the plural change rates, finds a plurality of the flicker frequencies at the time of the measurement of the brain potential used for calculation of the maximum value among the change rates and finds a first frequency using the flicker frequencies, and finds an absolute value of a difference between the first frequency and a second frequency, which is a flicker frequency threshold of the test subject when the test subject has no fatigue and determines that the test subject has mental fatigue when the absolute value is equal to or greater than a predetermined value.

\* \* \* \* \*